(12) United States Patent
Murayama et al.

(10) Patent No.: US 8,986,943 B2
(45) Date of Patent: *Mar. 24, 2015

(54) METHOD FOR PRE-TREATING SPECIMEN AND METHOD FOR ANALYZING SPECIMEN

(71) Applicant: Canon Kabushiki Kaisha, Tokyo (JP)

(72) Inventors: Yohei Murayama, Yokohama (JP); Hiroyuki Hashimoto, Yokohama (JP); Manabu Komatsu, Kawasaki (JP); Kazuhiro Ban, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/830,802

(22) Filed: Mar. 14, 2013

(65) Prior Publication Data

US 2013/0203105 A1    Aug. 8, 2013

Related U.S. Application Data

(62) Division of application No. 12/113,795, filed on May 1, 2008, now Pat. No. 8,415,116.

(30) Foreign Application Priority Data

May 7, 2007  (JP) ................... 2007-122301

(51) Int. Cl.
  *C12Q 1/02*   (2006.01)
  *G01N 1/30*   (2006.01)
  *G01N 1/00*   (2006.01)
  *G01N 1/31*   (2006.01)
  *G01N 1/28*   (2006.01)

(52) U.S. Cl.
  CPC .. *G01N 1/30* (2013.01); *G01N 1/31* (2013.01); *G01N 2001/282* (2013.01); *G01N 2001/317* (2013.01)
  USPC ............................... 435/29; 435/40.5; 356/36

(58) Field of Classification Search
  CPC .......... G01N 33/6848; G01N 33/4833; G01N 33/5082; G01N 33/54313; G06F 19/26; H01J 49/0004; H01J 49/142; H01J 49/40; H01J 49/0418; B82Y 15/00; C07K 14/4756
  See application file for complete search history.

(56) References Cited

U.S. PATENT DOCUMENTS

| | | | |
|---|---|---|---|
| 3,551,554 A * | 12/1970 | Herschler | ............ 424/9.4 |
| 4,877,745 A | 10/1989 | Hayes et al. | |
| 5,808,300 A | 9/1998 | Caprioli | |
| 6,184,973 B1 | 2/2001 | Baer et al. | |
| 6,707,038 B2 | 3/2004 | Ellson et al. | |
| 7,622,263 B2 | 11/2009 | Ban et al. | |
| 7,714,280 B2 | 5/2010 | Komatsu et al. | |
| 7,795,579 B2 | 9/2010 | Komatsu et al. | |
| 7,943,370 B2 | 5/2011 | Minami et al. | |
| 8,084,214 B2 | 12/2011 | Hashimoto et al. | |
| 2002/0195558 A1 | 12/2002 | Ellson et al. | |
| 2003/0175410 A1 | 9/2003 | Campbell et al. | |
| 2004/0219588 A1 | 11/2004 | Furuta | |
| 2006/0134793 A1 * | 6/2006 | Key et al. | ............ 436/63 |
| 2007/0105087 A1 | 5/2007 | Ban et al. | |
| 2008/0090267 A1 | 4/2008 | Komatsu et al. | |
| 2009/0005495 A1 | 1/2009 | Ban et al. | |
| 2009/0093373 A1 | 4/2009 | Kawaguchi et al. | |
| 2009/0148346 A1 | 6/2009 | Ban et al. | |
| 2011/0315871 A1 | 12/2011 | Komatsu et al. | |

FOREIGN PATENT DOCUMENTS

JP    2003-98060 A    4/2003

OTHER PUBLICATIONS

Hainfeld, et al., "Gold nanoparticles: a new X-ray contrast agent", The British Journal of Radiology, vol. 79, 2006, pp. 248-253.
Paciotti, et al., "Colloidal Gold Nanoparticles: A Novel Nanoparticle Platform for Developing Multifunctional Tumor-Targeted Drug Delivery Vectors", Drug Development Research, vol. 67, 2006, pp. 47-54.

* cited by examiner

*Primary Examiner* — Chris R Tate
*Assistant Examiner* — Douglas F White
(74) *Attorney, Agent, or Firm* — Fitzpatrick, Cella, Harper and Scinto

(57) ABSTRACT

A pre-treatment method for analyzing a specified portion in a specimen composed of a biological tissue includes the steps of preparing a specimen to be analyzed; determining a specified portion in the specimen; and applying an analysis inhibitor to a portion except the specified portion of the specimen using a droplet spray method.

13 Claims, 3 Drawing Sheets

METHOD FOR PRE-TREATING SPECIMEN AND METHOD FOR ANALYZING SPECIMEN

This application is a divisional of application Ser. No. 12/113,795, filed May 1, 2008, the contents of which are incorporated herein by reference.

BACKGROUND OF THE INVENTION

1. Field of the Invention

The present invention relates to a method for pre-treating a specimen and a method for analyzing a specimen.

2. Description of the Related Art

The importance of analysis of proteins which are gene products present in living organisms has come under close scrutiny with recent development in genome analysis.

The importance of expression and functional analysis of proteins has been pointed out, and development of an analysis method is being advanced.

Such a method basically includes a combination of (1) separation and purification by two-dimensional electrophoresis and high-performance liquid chromatography (HPLC) and (2) detection and analysis, such as radiometric analysis, optical analysis, mass spectrometry, and the like.

The basis of protein analysis techniques is called "proteome analysis" which aims at analyzing proteins derived from genes and actually functioning in living organisms and at investigating the functions of cells and the causes of diseases.

A typical analysis method includes the following:

(1) extraction of proteins from a biological tissue or cells to be examined;

(2) separation of the proteins by two-dimensional electrophoresis;

(3) analysis of the proteins or segments thereof by mass spectrometry such as a MALDI method (Matrix Assisted Laser Desorption/Ionization-Time of Flight Mass Spectrometry: MALDI-TOFMS); and (4) identification of the proteins using a database such as Genome Project.

For example, proteins involved in recurrence and metastasis of a cancer are being clarified by the proteome analysis, and the results thereof start to appear.

On the other hand, a technique relating to a pre-treatment step in the series of proteome analysis, for example, a pre-treatment technique for analyzing only target cells from a tissue sample containing normal cells and abnormal cells in a development stage of a cancer or the like, becomes very important.

Such a pre-treatment is generally performed by a technique of extracting target cells from a sample.

For example, U.S. Pat. No. 6,184,973 discloses an apparatus using microdissection.

The target cells are collected from a tissue sample using this apparatus according to the following procedures:

First, a glass slide on which a tissue sample has been fixed is placed at a center of a stage, and a sampling cap is moved using a cap transfer portion.

The glass slide is moved by manually operating the stage while the tissue sample is observed through an observation optical system of an inverted optical microscope to find the target cells in the tissue sample.

Next, the glass slide is positioned so that the target cells are at the center of a field of view.

Then, a laser beam is applied through the sampling cap, and only the target cells in the tissue sample are bonded using a thermoplastic portion of the sampling cap.

The sampling cap is separated from the glass slide to collect the target cells together with the sampling cap. Another known microdissection apparatus is of a type in which a target portion is cut out with a laser beam.

Apart from this, Japanese Patent Laid-Open No. 2003-098060 discloses a method of selectively collecting a target portion using a probe microscope.

The method disclosed in this document includes the following steps: coating a target sample with a coating material, forming an image of the coated sample using a probe microscope, curetting the target portion with a probe of the probe microscope, treating the target portion exposed by curettage, and selectively collecting a substance contained in the target portion.

Further, US 2004/0219588 discloses a method of analyzing only a target portion in a tissue sample by treating the target portion without physically taking out target cells from the tissue sample.

Specifically, in this method, an analytical reagent is adhered to a portion to be analyzed (the order of several 100 microns) by an ink jet method so that the portion is analyzed directly by a microscopic observation method or laser desorption/ionization mass spectrometry.

In the apparatus disclosed in U.S. Pat. No. 6,184,973, it is necessary to position a target cell at the center of the field of view while manually operating the stage for each of cells scattered at a plurality of points in the same tissue sample. In addition, it is necessary to apply a laser beam after the positioning operation, thereby requiring much labor and time for the work.

The technique using the probe microscope disclosed in Japanese Patent Laid-Open No. 2003-098060 includes coating the target portion with the coating agent, exposing the target portion by curetting with the probe, and analyzing the target portion. Therefore, reproducibility and analysis accuracy may be decreased.

Further, the method disclosed in US 2004/0219588 includes applying an analysis reagent to a specified region of a biological sample using an ink jet method and analyzing the specified region, and thus has limitations on the analysis reagent and analysis method.

SUMMARY OF THE INVENTION

The present invention provides a method for pre-treating a specimen in order to analyze a specified portion of the specimen composed of a biological tissue. The method includes the steps of preparing a specimen to be analyzed, determining a specified portion in the specimen, and applying an analysis inhibitor to a portion except the specified portion in the specimen using a droplet spray method.

The present invention also provides an analysis method for analyzing a specified portion of a specimen composed of a biological tissue. The method includes applying an analysis inhibitor, by a droplet spray method, to a portion except the specified portion to be analyzed to prepare a specimen, and analyzing the specified portion of the specimen.

The pre-treatment method of the present invention includes applying the analysis inhibitor to a portion except the specified portion using the liquid spray method and is thus capable of easy pre-treatment with high precision for analyzing only the specified region.

The analysis method of the present invention uses a specimen in which the analysis inhibitor is applied by the droplet spray method to a portion except the specified portion to be analyzed, and is thus capable of high-precision analysis of the specified portion without the influence of a portion except the specified portion.

Further features of the present invention will become apparent from the following description of exemplary embodiments with reference to the attached drawings.

DESCRIPTION OF THE EMBODIMENTS

The present invention will be described in detail below.

A specimen pre-treatment method provided by the present invention is a pre-treatment method for analyzing a specified portion of a specimen composed of a biological tissue. This method includes the steps of preparing a specimen to be analyzed, determining a specified portion in the specimen, and applying an analysis inhibitor to a portion except the specified portion in the specimen using a droplet spray method.

In the present invention, the term "biological tissue" represents a tissue constituting a portion of a living organism.

Types of the tissue include connective tissues of bone, cartilage, muscle, sinew, and the like, blood vessel, nerve, skin, hair, and various organs. The various organs include eyes, lung, kidney, heart, lever, pancreas, spleen, alimentary canal including intestine, bladder, ovary, and testis. The tissues also include tissues (e.g., embryonic tissue) in an occurrence stage or in the course of organization, and tissues mutated by various conditions, for example, diseased tissues.

The tissues can be derived from animals other than humans, such as reptiles, amphibians, fishes, birds, mammals, and the like, or humans. However, it is practically preferred to use human cells or the like.

In the present invention, a specified portion to be analyzed can be set to a specified cell in a biological tissue section.

Figure 1:
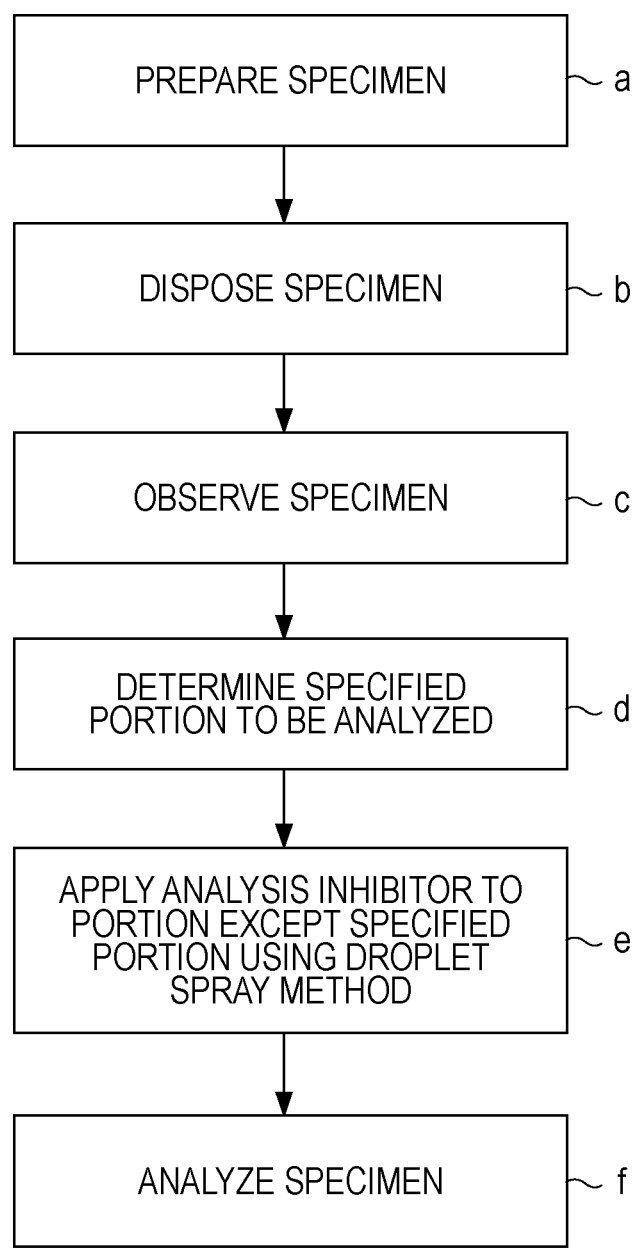
FIG. 1 is a drawing showing steps in an example of a pre-treatment method according to an embodiment of the present invention.

FIG. 1 is a drawing showing steps of an example of a pre-treatment method according to the present invention.

In step (a), a specimen composed of a biological tissue is prepared. In this case, the specimen is a tissue section according to an analytical method for the specimen. The biological tissue section can be appropriately selected according to the purpose of analysis, but a diseased tissue can be used as an example.

In step (b), the specimen is disposed on a substrate used for pre-treatment. The substrate used is preferably a substrate which can be used for analysis, but another substrate used for a purpose other than analysis can be used.

In step (c), the specimen is observed. The observation may be performed by a method which permits observation of a specified portion to be analyzed in the specimen, and an optical microscope or a CCD camera may be used for observation.

In step (d), the specified portion to be analyzed is determined. The specified portion to be analyzed is a portion desired to be analyzed in the specimen, and, for example, a diseased tissue can be used as the specified portion. The specified portion can be determined by, for example, an optical method. The specified portion may be determined by an observer on the basis of the decision on surface conditions of the specimen or may be determined by an observer or automatically on the basis of a surface image of the specimen which is processed by a specified program.

When the specified portion is determined by the observer, the specified portion can be manually determined by the observer under observation with an optical microscope and can be recorded as a dot on an x-y coordinate.

Alternatively, the specified portion can be automatically determined using contrast differences in a digital image formed by observation with an optical microscope and can be recorded as a dot on an x-y coordinate.

When the surface conditions of the specimen are determined, the specified portion to be analyzed can be easily discriminated from other portions by labeling, staining, or the like.

In step (e), an analysis inhibitor is applied by a droplet spray method to a portion except the specified portion to be analyzed. In this step, the analysis inhibitor is applied to a surface of the specimen except the portion to be analyzed so that a substance present on the surface is not analyzed. Therefore, a micro portion such as a cell to be analyzed can be analyzed directly without being collected from the specimen and unnecessary signals from portions other than the analyzed portion can be removed, thereby improving analysis accuracy.

The analysis inhibitor can be selected according to the purpose of analysis and the analysis method.

Examples of the analysis inhibitor used in the present invention include an ionization inhibitor, an X-ray absorber, an ultraviolet absorber, a visible light absorber, an infrared absorber, a terahertz light absorber, and the like.

An example of the ionization inhibitor is a nonvolatile material (compound) containing at least one of lithium, sodium, potassium, and calcium. These elements are known as elements which can be easily ionized. Therefore, when a material containing at least one of the elements is applied to a surface of the specimen, ionization of molecules in the specimen which are positioned directly below the material is inhibited because the element contained is selectively ionized.

Therefore, in analysis using ionization, such as mass spectrometry, when the inhibitor is applied to a portion except the specified portion to be analyzed in the specimen, a mass spectrum derived from a portion other than the analyzed portion is due to only the element ions. Thus, mixing of unnecessary mass spectra due to proteins present in the portion can be decreased, thereby permitting analysis with high precision.

An example of the X-ray absorber is a material containing at least one of elements with atomic numbers of 40 or larger, such as iodine, barium, lead, and the like. Since this element group has high X-ray absorption coefficients, when the material is applied to a portion other then the portion to be analyzed in the specimen, the element selectively absorbs X-ray in transmission X-ray analysis. Therefore, the resultant transmission X-ray energy spectrum does not include signals derived from that portion, thereby permitting analysis with high precision.

An example of an absorber for light in other wavelength regions, such as ultraviolet light, visible light, infrared light, and terahertz light, is a material containing at least one selected from the group consisting of synthetic polymer compounds, such as a surfactant, a dye, a metal complex, and the like. Since such a material is generally easily fixed and contains various functional groups, it easily absorbs light. Therefore, for the same reason as that of X-ray analysis, the resultant transmitted light spectrum of the specified analyzed portion does not include signals depending on portions other than the specified portion, thereby permitting analysis with high precision. The examples of the X-ray absorber also include materials sensitive to light in other wavelength regions, such as ultraviolet light, visible light, infrared light, and terahertz light, and these materials can also be used.

The droplet spray method for applying the analysis inhibitor uses a droplet applying method generally used for a so-called ink jet printer. Such a method is roughly divided into a type using heat energy for ejecting droplets and a type using a piezoelectric element. However, in the present invention, the droplet applying method may be either of these types.

In the present invention, the droplet spray method used in a so-called ink jet method can apply the analysis inhibitor to portions excluding a micro portion such as a portion corresponding to a cell. When the analysis inhibitor is applied, it is preferred to apply a solution at as a low concentration as possible according to the inhibitor used so as to prevent clogging of a spray nozzle.

Although the amount of the inhibitor applied is not particularly limited, the inhibitor is preferably applied to all portions except the portion to be analyzed in the specimen so that the portions are not exposed in the uppermost surface. However, it is necessary to pay attention to avoid spreading of droplets to the target portion to be analyzed when droplets containing the analysis inhibitor are applied to the specimen.

In addition to the application of the analysis inhibitor, if required, an analytical reagent may be applied to the target portion to be analyzed. The analytical reagent may be applied before, after, or at the same time as the step of applying the analysis inhibitor. As the analytical reagent, a reagent for improving analytical sensitivity can be used.

The above-described steps (a) to (e) are pre-treatment steps.

After the pre-treatment steps, the specimen is analyzed in next step (f).

Examples of an analysis method include mass spectrometry represented by a MALDI (Matrix Assisted Laser Desorption/Ionization) method or a TOF-SIMS (Time of Flight Secondary Ion Mass Spectrometry) method, an X-ray transmission or diffraction method, a reflection/absorption method using ultraviolet light, visible light, infrared light, terahertz light, or the like.

However, the analysis method may be selected according to the purpose of analysis of the specified portion of the specimen, and the method is not limited to the above-described methods. Although a measurement region is generally specified in analysis, the pre-treatment brings a portion except the specified portion to be analyzed into a state not to be analyzed in the present invention. Therefore, direct measurement may be performed for portions including the specified portion. In addition, even if the area of the measurement region is larger than that of the specified portion, direct measurement of the specimen can be conducted for the same reason as described above.

Specifically, in analyzing a cell, the measurement region may be in the order of, for example, 100 microns or 1 millimeter, while a cell has a diameter in the order of several tens of microns.

When the specimen is analyzed after the pre-treatment of the present invention, the obtained measurement results do not contain signals derived from portions other than the target portion analyzed or such signals are greatly suppressed, thereby permitting analysis with high precision.

Hereinafter, the present invention is described in further detail with reference to examples. However, these are only examples of the present invention, and the present invention is not limited to these examples.

EXAMPLES

Example 1

An example of pre-treatment performed for TOF-SIMS analysis of only specified cells in a tissue section sample is described.

Figure 5:
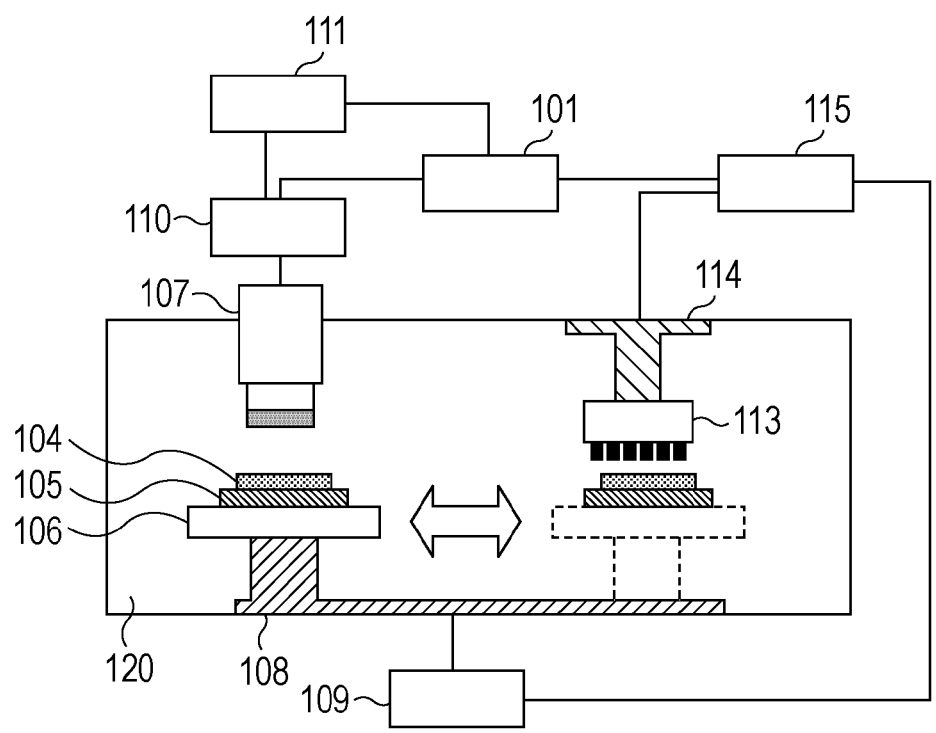
FIG. 5 is a conceptual view showing a pre-treatment apparatus which can be applied to a method of the present invention.

FIG. 5 shows a pre-treatment apparatus used in this example. In the apparatus shown in FIG. 5, a substrate 105 which holds a specimen 104 is mounted on a stage 106 in a container 120. In FIG. 5, reference numeral 108 denotes a moving device for moving the stage 106; reference numeral 107, an optical observation device; reference numeral 113, an ink jet head serving as a liquid spray device, which is connected to a head moving mechanism 114; and reference numeral 109, a position control mechanism for the stage 106. The optical observation device 107 is connected to a mechanism 110 for recording an image obtained by optical observation, and the image recording mechanism 110 is connected to a mechanism (automatic or manual) 111 for processing the image to determine a region to which droplets containing the analysis inhibitor are applied. Reference numeral 101 denotes an interface for connecting a control mechanism 115 of the ink jet head 113, the mechanism 111 for determining the region where the droplets are applied, and the image recording mechanism 110.

The specimen 104 is a diseased tissue section which is obtained by slicing with a microtome under refrigeration. The specimen 104 is fixed on the substrate 105. The substrate 105 is prepared by washing a silicon (Si) substrate not containing impurities with acetone and deionized water in that order and depositing gold (Au) to 100 nm.

Figure 2:
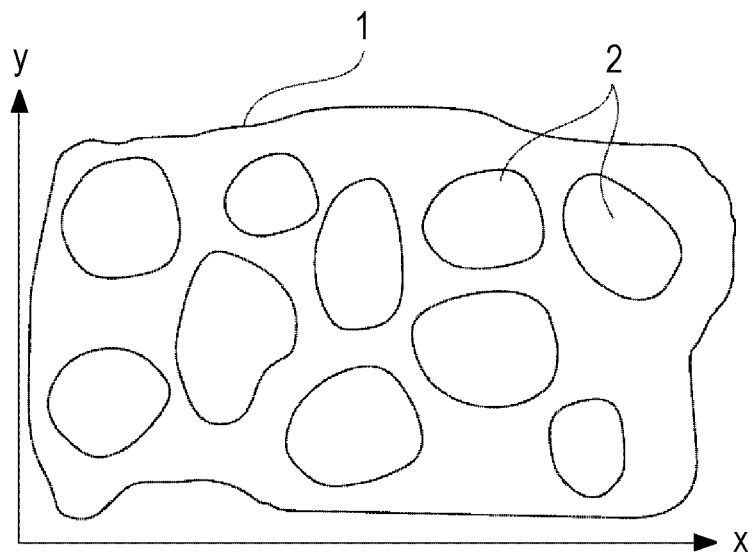
FIG. 2 is a drawing of an example of an image obtained by observing a specimen.

The specimen 104 fixed on the substrate 105 is observed with an optical microscope 107, and a digital image is formed by the image recording mechanism 110. As a result, the digital image shown in FIG. 2 is obtained. In FIG. 2, reference numeral 1 denotes a diseased tissue section, and reference numeral 2 denotes a cell in the diseased tissue section.

Figure 3:
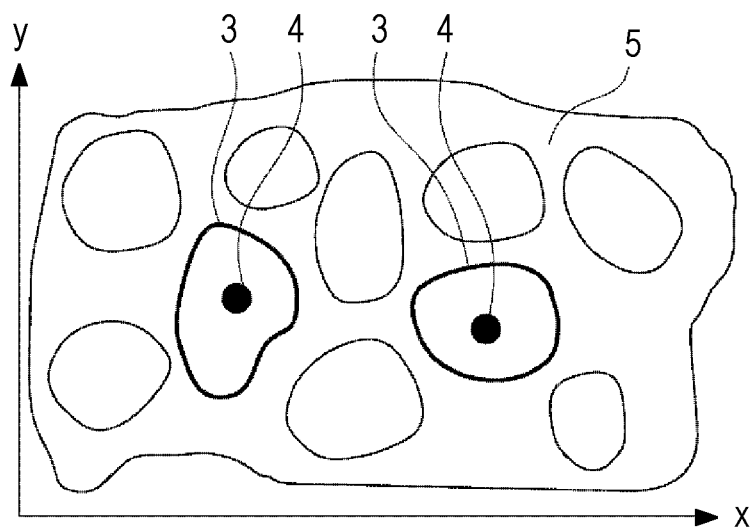
FIG. 3 is a drawing of an example of an image obtained by observing a specimen, showing an analysis target portion and a portion other than the target portion.

On the basis of contrast differences in the resultant digital image, as shown in FIG. 3, the diseased cells to be analyzed are recognized by the mechanism 111 which determined the region where the droplets are applied, and the contours of the cells and the xy coordinates of the centers thereof are recorded.

In FIG. 3, reference numeral 3 denotes the diseased cell, and reference numeral 4 denotes the center of the diseased cell.

The portion where the analysis inhibitor is applied by the ink jet method is also recognized by the mechanism 111 as a drawn image for printing as shown by reference numeral 5 in FIG. 3.

Figure 4:
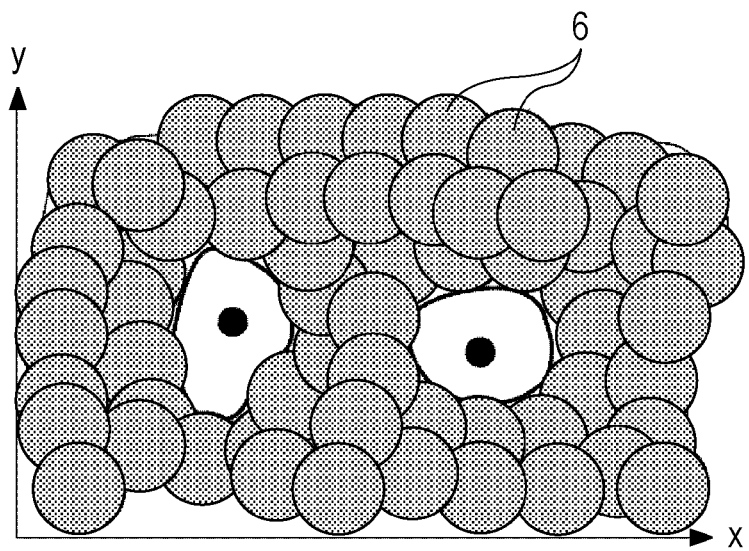
FIG. 4 is conceptual view showing a state in which an analysis inhibitor is applied as droplets (dots) to a portion other than an analysis target portion.

Next, the substrate 105 on which the specimen section 104 is fixed is moved to a position below the ink jet head 113, and droplets containing the analysis inhibitor are applied to the portion 5 (in FIG. 3) except the target portion to be analyzed from the ink jet head 113. As the analysis inhibitor, sodium carbonate ($Na_2CO_3$) is used, and a 0.1 wt % aqueous solution of the inhibitor is charged in an ink tank. As the ink jet head, a printer head of commercial bubble jet (trade name) printer PIXUS990i manufactured by CANON KABUSHIKI KAISHA is modified for experiments and used. The amount of the aqueous solution contained in each of the droplets discharged from the printer head used is 4 pl. The droplets become dots of about 30 microns in diameter when applied to an object. Therefore, in consideration of the diameter, it is necessary to determine the pitch width between dots so that the entire surface of the region where the analysis inhibitor is applied is covered with the droplets. The droplet discharge is controlled by the control mechanism 115 of the head so that the droplets are discharged at a pitch width of 15 microns between the dots. FIG. 4 is a conceptual view of dots when the analysis inhibitor is applied by the ink jet method. In FIG. 4, reference numeral 6 denotes overlapping dots.

After the application of the $Na_2CO_3$ aqueous solution is completed, the specimen is allowed to stand at room temperature and normal pressure for 3 minutes, and then the analytical reagent is applied to the diseased cells to be analyzed. As the analytical reagent, a 0.4 µM diluted aqueous solution of a digestive enzyme, trypsin, is used and charged in an ink tank other than the ink tank of the $Na_2CO_3$ aqueous solution. The droplets of the aqueous solution containing the digestive enzyme are applied to the xy coordinate centers of the diseased cells determined in FIG. 3. In consideration of the fact that the upper limit of detectable mass number of TOF-SIMS analysis is about 2,000, the digestive enzyme is used for decomposing the proteins contained in the diseased cells into peptides. The mass numbers of peptides produced by decomposition with the digestive enzyme range from about 500 to 2,000, and the mass numbers for the TOF-SIMS analysis range from 500 to 2,000. After the application of the digestive enzyme, the specimen is maintained at room temperature and a humidity of 80% or less for 30 minutes.

Then, the specimen pre-treated as described above is separated together with the substrate and used directly as a sample for TOF-SIMS analysis. The thus-prepared sample assumes a state in which only the diseased cells in the diseased tissue are isolated from other normal cells without being mechanically separated therefrom. Therefore, in the TOF-AIMS analysis, few unnecessary signals are mixed from the peripheral region, thereby improving the precision of identification of a parent protein by detection of the peptides present in the diseased cells.

Example 2

An example of pre-treatment performed for X-ray analysis of only specified cells in a tissue section sample is described below.

A specimen is a diseased tissue section which is obtained by slicing with a microtome under refrigeration. The specimen is fixed on a substrate composed of a polyimide film.

As in Example 1, the diseased tissue section fixed on the substrate is observed with an optical microscope to form a digital image. On the basis of contrast differences in the resultant digital image, the diseased cells to be analyzed are automatically recognized, and the contours of the cells and the xy coordinates of the centers thereof are recorded. In this automatic recognition, a portion to which the analysis inhibitor is applied by liquid spray is also recognized as a drawn image for printing.

Next, droplets containing the analysis inhibitor are applied, by the liquid spray method, to a portion except the analysis targets recognized as described above. As the analysis inhibitor, a 10 wt % aqueous solution of an iodobenzene derivative is used and charged in an ink tank. The analysis inhibitor is applied using the same apparatus as in Example 1.

After the application of the aqueous solution containing an iodobenzene derivative is completed, the specimen is allowed to stand at room temperature and normal pressure for 3 minutes. Then, the specimen pre-treated as described above is separated together with the substrate and used directly as a sample for X-ray analysis. The thus-prepared sample assumes a state in which only the diseased cells in the diseased tissue are isolated from other normal cells without being mechanically separated therefrom.

Namely, when a transmission X-ray spectrum and a projected image are detected by vertically irradiating the surface of the sample with X-rays, the presence of unnecessary signals due to portions other than the analysis targets is reduced, thereby permitting high-precision analysis of proteins present in the diseased cells.

While the present invention has been described with reference to exemplary embodiments, it is to be understood that the invention is not limited to the disclosed exemplary embodiments. The scope of the following claims is to be accorded the broadest interpretation so as to encompass all modifications and equivalent structures and functions.

This application claims the benefit of Japanese Application No. 2007-122301 filed May 7, 2007, which is hereby incorporated by reference herein in its entirety.

What is claimed is:

1. A treatment method for a specimen composed of a biological tissue for analyzing the specimen using at least one of an ion, an X-ray, an ultraviolet, a visible light, an infrared, and a terahertz light, the method comprising the step of:

applying an analysis inhibitor to a portion other than a target portion of the specimen so as not to apply the analysis inhibitor to the specified target portion, the target portion being a predetermined portion to be analyzed in a portion to be measured, wherein the analysis inhibitor contains at least one of an ionization inhibitor, an X-ray absorber, an ultraviolet absorber, a visible light absorber, an infrared absorber, and a terahertz light absorber, and wherein the analysis inhibitor is a substance having a function to reduce an amount of signals which are derived from a substance existing in the portion to be measured.

2. The treatment method according to claim 1, wherein the target portion is composed of a specified cell in a biological tissue section.

3. The treatment method according to claim 1, wherein the ionization inhibitor contains a nonvolatile compound containing at least one of lithium, sodium, potassium, and calcium.

4. The treatment method according to claim 1, wherein the X-ray absorber contains an element with an atomic number of 40 or larger.

5. The treatment method according to claim 1, wherein one of the ultraviolet absorber, the visible light absorber, the infrared absorber, and the terahertz light absorber contains a polymer compound.

6. The treatment method according to claim 1, further comprising applying an analytical reagent to the target portion.

7. A method of making a treated specimen for analyzing a specimen using at least one of an ion, an X-ray, an ultraviolet, a visible light, an infrared, and a terahertz light, the method comprising the steps of:
- preparing a specimen composed of a biological tissue; and
- applying an analysis inhibitor to a portion other than a target portion of the specimen so as not to apply the analysis inhibitor to the specified target portion, the target portion being a predetermined portion to be analyzed in a portion to be measured,
- wherein the analysis inhibitor contains at least one of an ionization inhibitor, an X-ray absorber, an ultraviolet absorber, a visible light absorber, an infrared absorber, and a terahertz light absorber, and
- wherein the analysis inhibitor is a substance having a function to reduce an amount of signals which are derived from a substance existing in the portion to be measured.

8. The treatment method according to claim 1, wherein the analysis inhibitor is applied to all portions except for the target portion of the specimen.

9. The treatment method according to claim 1, wherein the ionization inhibitor is a substance which is ionized more preferentially than a substance existing in the portion to be measured other than the portion to be analyzed in the specimen.

10. The treatment method according to claim 1, wherein the x-ray absorber is a substance which absorbs an x-ray more preferentially than a substance existing in the portion to be measured other than the portion to be analyzed in the specimen.

11. The treatment method according to claim 1, wherein the analysis inhibitor is applied to a portion not to be analyzed along a boundary between the portion to be analyzed and the portion not to be analyzed so as to cover an outer periphery of the portion to be analyzed.

12. The treatment method according to claim 1, wherein the signal is at least one kind of signal selected from secondary ion, transmitted light and reflected light.

13. The treatment method according to claim 1, wherein the specified portion is determined by observation with an optical microscope and recorded as a dot on an x-y coordinate.

* * * * *